United States Patent
Valle et al.

(10) Patent No.: US 6,509,185 B1
(45) Date of Patent: Jan. 21, 2003

(54) MUTANT APRE PROMOTOR

(75) Inventors: Fernando Valle, Burlingame, CA (US); Eugenio Ferrari, San Bruno, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/479,494

(22) Filed: Jan. 7, 2000

(51) Int. Cl.[7] .......................... C12N 1/20; C12N 15/00; C12N 15/09; C12P 21/06; C07H 21/04

(52) U.S. Cl. ....................... 435/252.31; 435/252.3; 435/471; 435/320.1; 435/69.1; 536/23.1; 536/24.1

(58) Field of Search .............................. 536/23.1, 24.1; 435/69.1, 252.3, 471, 252.31, 320.1

(56) References Cited

PUBLICATIONS

Jan, et al. FEMS Microbiology Letters, 183: 9–14, Feb. 2000.*
Park, et al. Journal of Bacteriology, vol. 171, No. 5, pp. 2657–2665, May 1989.*
Ferrari, et al. Journal of Bacteriology, vol. 170, No. 1, pp. 289–295, Jan. 1988.*
Bakhiet, Nouna and Donald P. Stahly, "Studies on Transfection and Transformation of Protoplasts of *Bacillus larvae, Bacillus subtilis,* and *Bacillus popilliae,*" Applied and Environmental Microbiology, pp. 577–581, Mar. 1985.
Bron, Sierd, *Molecular Biological Methods for Bacillus,* ed. Harwood and Cutting, John Wiley & Sons, pp. 75–174, 1990.
Chang, Shing et al., "High Frequency Transformation of *Bacillus subtilis* Protoplasts," Molec. Gen. Genet., vol. 168, pp. 111–115, 1979.
Contente, Sara et al., "Marker Rescue Transformation by Linear Plasmid DNA in *Bacillus subtilis,*" Plasmid, vol. 2, pp. 555–571, 1979.
Debabov, V.G., "The Industrial Use of Bacilli," *The Molecular Biology of the Bacilli,* Dubnau, D.A., ed., Academic Press, vol. 1, pp. 331–370, 1982.
Fischer, Hans–Martin, et al., "Introduction of plasmid pC194 into *Bacillus thuringiensis* by protoplast transformation and plasmid transfer," Arch. Microbiol., vol. 139, pp. 213–217, 1984.
Genex Corp., Sequence Accession No. N60475, Database EMBL Online, "Sequence of the apr 'BSU! gene encoding subtilisin" XP–002166627, Aug. 24, 1991.
Haima, Peter, et al., "Novel plasmid marker rescue transformation system for molecular cloning in *Bacillus subtilis* enableing direct selection of recombinants," Mol. Gen. Genet, vol. 223, pp. 185–181, 1990.
Henner, Dennis et al., "Localization of *Bacillus subilis* sacU(Hy) Mutations to Two Linked Genes with Similarities to the Conserved Procaryotic Family of Two–Component Signalling System," Journal of Bacteriology, vol. 170, No. 11, pp. 5102–5109, Nov. 1988.
Henner, Dennis, et al., "Location of theTargets of the hpr–97, sacU32(Hy), and sacQ36(Hy)Mutations in Upstream Regions of the Subtilisin Promoter," Journal of Bacteriology, vol. 170, No. 1, pp. 296–300, Jan. 1988.

(List continued on next page.)

*Primary Examiner*—David Guzo
*Assistant Examiner*—Gerald G. Leffers
(74) *Attorney, Agent, or Firm*—Genecor International, Inc.

(57) ABSTRACT

The present invention provides a mutant aprE promoter and methods for the production of a desired protein in a Bacillus host cell, which comprises the mutant aprE promoter. The present invention provides the sequence of a preferred aprE mutant promoter, which provided for a 100-fold increase in the production of a protein from *Bacillus subtilis.*

23 Claims, 1 Drawing Sheet

OTHER PUBLICATIONS

Holubova, I., et al., "Transfer of Liposome–Encapsulated Plasmid DNA to *Bacillus subtilis* Protoplasts and Calcium–Treated *Escherichia coli* Cells," Folia Microbiol. vol. 30, pp. 97–100, 1985.

Kunst, F., et al., "The complete genome sequence of the Gram–positive bacterium *Bacillus subtilis*," Nature, vol. 390, Nov. 20, 1997.

Mann, Stephen P., et al., "Transformation of Bacillus spp.: an Examination of the Transformation of Bacillus Photoplasts by Plasmids pUB110 and pHV33," Current Microbiology, vol. 13, pp. 191–195, 1986.

McCready, Paula M., et al., "*Bacillus subtilis* SenS exerts its activity through a site in the 5' flanking region of the aprE promotor," Journal of General Microbiology, vol. 138, pp. 2069–2074, 1992.

McDonald, Karen Orzech, et al., "Plasmid Transformation of *Bacillus sphaericus* 1593," Journal of General Microbiology, vol. 130, pp. 203–208, 1984.

Merino, Enrique, et al., "BioFeedback, A General,PCR–Based Method for Single or Combinatorial Oligonucleotide–Directed Mutagenesis on pUC/M13 Vectors," BioTechniques, vol. 12, No. 4, pp. 508–510, 1992.

Olmos, J., et al., "A Functional SpoOA is required for maximal aprE expression in *Bacillus subtilis*," FEBS Letters, vol. 381, pp. 29–31,1996.

Oyama,Hiroshi, et al., "Secretion of *Escherichia coli* Aminopeptidase P in *Bacillus subtilis* Using the Prepro–Structure Coding Region of Subtilisin Amylosacchariticus," Journal of Fermentation and Bioengineering, vol. 68, No. 4., pp. 289–292, 1989.

Papas, Takis, S., et al., ed. *Gene Amplification and Analysis*, Elsevier, vol. 3, pp. 64–87, 1983.

Perego, Marta, et al., "Sequence Analysis and Regulation of the hpr Locus, a Regulatory Gene for Protease Production and Sporulation in *Bacillus subtilis*," Journal of Bacteriology, vol. 170, No. 6, pp. 2560–2567, Jun., 1988.

Ross, Wilma, et al., "A Third Recognition Element in Bacterial Promoters: DNA Binding by the αSubunit of RNA Polymerase," Science, vol. 262, pp. 1407–1413, Nov. 26, 1993.

Sanger, F., et al., "DNA sequencing with chain–terminating inhibitors," Proc. Natl. Acad. Sci. USA, vol. 74, No. 12, pp. 5463–5467, Dec., 1977.

Smith, Michael D., et al., "Photoplast Transformation in Coryneform Bacteria and Introduction of an α–Amylase Gene from *Bacillus amyloliquefaciens* into *Brevibacterium lactofermentum*," Applied and Environmental Microbiology, vol. 51, No. 3, pp. 634–639, Mar. 1986.

Sonenshein, Abraham L., "Metabolic Regulation of Sporulation and Other Stationary–Phase Phenomena," *Regulation of Procaryotic Development*, Smith, I. et al, ed., American Society for Microbiology, Washington, D.C., pp. 109–130, 1989.

Stahl, Mark L., et al., "Replacement of the *Bacillus subtilis* Subtilisin Structural Gene with an In Vitro–Derived Deletion Mutation," Journal of Bacteriology, vol. 158, No. 2, pp. 411–418, May, 1984.

Valle, Fernando, et al., "Subtilisin: a Redundantly Temporally Regulated Gene?" Regulation of Procaryotic Deveploment, Smith, I. et al., ed., American Society for Microbiology, Washington, D.C. pp. 131–146, 1989.

Vorobjeva, I.P., et al., "Transformation of Bacillus Megaterium Protoplasts by Plasmid DNA," FEMS Microbiology Letters, vol. 7, pp. 261–263, 1980.

Walsh, Kenneth, et al.,"Characterzation of rate–controlling steps in vivo by use of an adjustable expression vector," Proc. Natl. Acad. Sci. US.A., vol. 82, pp. 3577–3581, Jun. 1985.

Weinrauch, Y., et al., "Plasmid Marker Rescue Transformation in *Bacillus subtilis*," Journal of Bacteriology, vol. 154, No. 3, pp. 1077–1087, Jun. 1983.

Weinrauch, Y., et al., "Plasmid Marker Rescue Transformation Proceeds by Breakage–Reunion in *Bacillus subtilis*, "Journal of Bacteriology, vol. 169, No. 3, pp. 1205–1211, 1987.

Wong, Sui–Lam, et al., "The subtilisin E gene of *Bacillus subtilis* is transcribed from a $\sigma^{37}$ promoter in vivo," Proc. Natl. Acad. Sci. USA, vol. 81, pp. 1184–1188, Feb. 1984.

Yang, Maria Y., et al., "Cloning of the Neutral Protease Gene of *Bacillus subtilis* and the Use of the Cloned Gene to Creat an In Vitro–Derived Deletion Mutation," Journal of Bacteriology, vol. 160, No. 1, pp. 15–21, Oct., 1984.

Zubowski, Mark M., "Production of Commerically Valuable Products," *Biology of bacilli: applications to industry*, Doi, R.H., et al.,ed., Butterworth–Heinemann, Stoneham, Massachusetts, pp. 311–337, 1992.

* cited by examiner

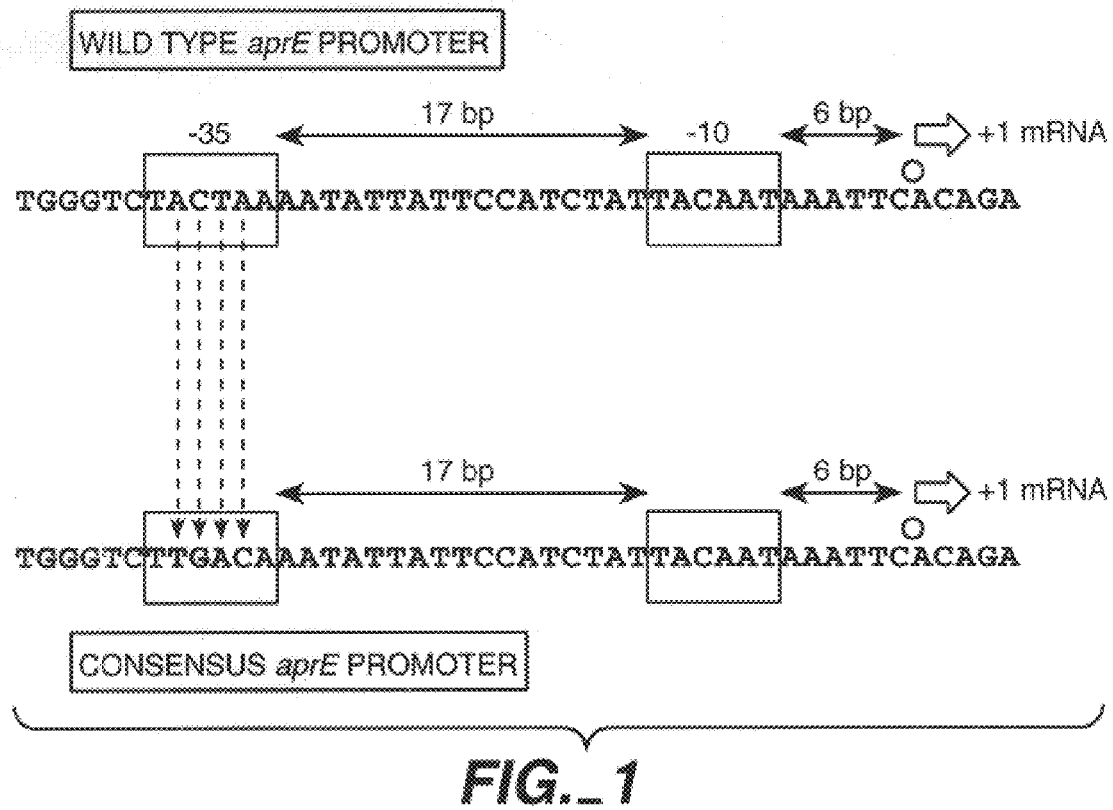
FIG._1
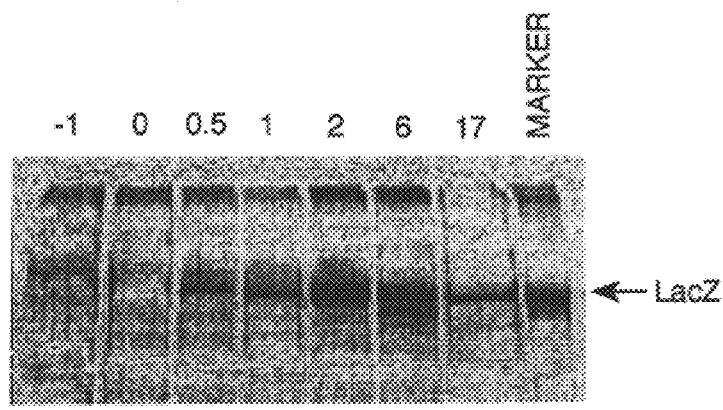
FIG._2

SEQUENCE LISTING

<160> NUMBER OF SEQ ID NOS: 6

<210> SEQ ID NO 1
<211> LENGTH: 46
<212> TYPE: DNA
<213> ORGANISM: Artificial Sequence
<220> FEATURE:
<223> OTHER INFORMATION: promoter

<400> SEQUENCE: 1
tgggtcttga caaatattat tccatctatt acaataaatt cacaga          46

```
<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
atatgtggtg ccgaaacgct ctggggtaac                                    30

<210> SEQ ID NO 3
<211> LENGTH: 52
<212> TYPE: DNA
<213> ORGANISM: Artificial Sequence
<220> FEATURE:
<223> OTHER INFORMATION: primer

<400> SEQUENCE: 3
ctcaaaaaaa tgggtctact aaaatattat tccatctatt acaataaatt ca           52

<210> SEQ ID NO 4
<211> LENGTH: 52
<212> TYPE: DNA
<213> ORGANISM: Artificial Sequence
<220> FEATURE:
<223> OTHER INFORMATION: primer

<400> SEQUENCE: 4
tgaatttatt gtaatagatg gaataatatt ttagtagacc cattttttg ag            52

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
cttttcttca tgcgccgtca gcttttctc                                     30

<210> SEQ ID NO 6
<211> LENGTH: 46
<212> TYPE: DNA
<213> ORGANISM: Bacillus sp.

<400> SEQUENCE: 6
tgggtctact aaaatattat tccatctatt acaataaatt cacaga                  46
```

MUTANT APRE PROMOTOR

FIELD OF THE INVENTION

The present invention is in the field of molecular biology and relates to the production of proteins in Bacillus species. In particular the present invention relates to a mutant aprE promotor and its use in methods for the production of proteins.

BACKGROUND OF THE INVENTION

Genetic engineering has allowed the improvement of microorganisms used as industrial bioreactors, cell factories and in food fermentations. The Bacillus genera produce and secrete a large number of useful proteins and metabolites (Zukowski 1992 Zukowski M M (1992) Production of commercially valuable products. In: Doi R H, McGlouglin M (eds) Biology of bacilli: applications to industry. Butterworth-Heinemann, Stoneham. Mass pp 311–337). The most common bacilli used in industry are *B. licheniformis, B. amyloliquefaciens* and *B. subtilis*. Furthermore, because of its GRAS (generally recognized as safe) status, *B. subtilis* is a natural candidate for the production of proteins utilized in the food and phamaceutical industries.

The aprE gene of *B. subtilis* codes for the extracellular protease subtilisn, a valuable enzyme manufactured by the biotechnology industry (Debadov V G (1982) The Industrial Use of Bacilli. In: Dubnau D A (ed) The Molecular Biology of the Bacilli. Academic Press: New York/London, vol 1, pp 331–370). The development of recombinant protein production systems using *B. subtilis* as a host organism, especially those driven by the subtilisin promoter, provides an important tool for research and commercial production in this area (Oyama et al. (1989) Secretion of *Escherichia coli* Aminopeptidase P in *Bacillus subtilis* using the Prepro-Structure Coding Region of Subtilisin Amylosaccharticus. J. Ferment. Bioeng. 68: 289–292). Although subtilisin synthesis is not required for sporulation (Stahl and Ferrari (1984) Replacement of the *Bacillus subtilis* Subtilisin Structural Gene With an In Vitro-Derived Deletion Mutation. J Bacteriol. 158: 411–418), its production is triggered by mechanisms common to those events responsible for the sporulation initiation, and hence, it has served as a model for developmentally-associated gene expression (Sonenshein A L (1989) Metabolic Regulation of Sporulation and Other Stationary-Phase Phenomenon. In: Smith I, Slepecky R A, Setlow P (eds) Regulation of Procaryotic Development. American Society for Microbiology, Washington, D.C. pp 109–130). The aprE gene is transcribed by sigma A ($\sigma^A$) and its expression is highly controlled by several regulators, such as: DegU/DegS, AbrB, Hpr and SinR (Valle and Ferrari (1989) In: Smith I, Slepecky R A, Setlow P (eds) Regulation of Procaryotic Development. American Society for Microbiology. Washington, D.C. pp 131–146). A consensus sigma A promoter has been identified (Helman et al., 1995, Nucleic Acid Research, Vol. 23, pp. 2351–2360). In spite of advances in the understanding of production of proteins in host cells, there remains a need for methods for increasing expression of proteins in host cells, such as Bacillus host cells.

SUMMARY OF THE INVENTION

The present invention relates to the use of a mutant aprE promoter in the production of proteins. The present invention is based upon the unexpected finding that a hundred fold increase in the production of a desired protein occurred in a host cell which contained the mutant aprE promoter. The present invention is also based upon the unexpected finding that the mutant aprE promoter having the nucleotide sequence as shown in SEQ ID NO:1 was able to enhance transcription of both heterologous and homologous proteins and remained regulatable during production of the proteins. Accordingly, the present invention provides an isolated mutant aprE promoter and in another embodiment, provides an isolated mutant aprE promoter having the nucleotide sequence as given in SEQ ID NO: 1. The present invention also provides for host cells comprising an isolated mutant aprE promoter and methods for using such host cells to produce desired proteins. In one embodiment, the host cell is a Bacillus species and in another embodiment, the Bacillus species includes *B. licheniformis, B. lentus, B. brevis, B. stearothermophilus, B. alkalophilus, B. amyloliquefaciens, B. coagulans, B. circulans, B. lautus* and *Bacillus thuringiensis*. In another embodiment, the desired protein is subtilisn.

In yet another embodiment, the host cell comprising an isolated mutant aprE promoter, and in particular the isolated mutant aprE promoter of SEQ ID NO: 1, further comprises nucleic acid encoding a desired protein which may be homologous or heterologous to the host cell. The nucleic acid may encode therapeutically significant proteins or peptides, such as growth factors, cytokines, ligands, receptors and inhibitors, as well as vaccines and antibodies. The nucleic acid may encode commercially important industrial proteins or peptides, such as proteases, including subtilisn, carbohydrases such as amylases and glucoamylases, cellulases, oxidases and lipases. The nucleic acid may be a naturally occurring gene, a mutated gene or a synthetic gene. Examples of industrial proteins include enzymes such as hydrolases including proteases, cellulases, amylases, carbohydrases, and lipases; isomerases such as racemases, epimerases, tautomerases, or mutases; transferases, kinases and phophatases. In one embodiment, the protein is heterologous to the cell and in another it is homologous to the cell. In one illustrative embodiment disclosed herein, the protein is β-galactosidase and in another illustrative embodiment disclosed herein, the protein is subtilisn.

The present invention provides methods for producing a desired protein in a Bacillus species comprising, culturing a Bacillus comprising an isolated aprE promoter said Bacillus further comprising nucleic acid encoding the desired protein and optionally recovering said desired protein. In one embodiment, the isolated mutant aprE promoter has the sequence as shown in SEQ ID NO:1. In one embodiment of the method, said nucleic acid encoding the desired protein is integrated into the Bacillus genome and in another embodiment, nucleic acid encoding the desired protein is present on a replicating plasmid. The present invention also provides for methods for producing host cells comprising an isolated mutant aprE promoter.

BRIEF DESCRIPTION OF THE DRAWINGS

FIG. 1 Comparison of the DNA sequence of the wild type (SEQ ID NO:6) and mutated (SEQ ID NO:1) aprE promoter mutated bases are indicated with the dotted arrows (only the relevant sequence of the aprE regulatory region is depicted). The separation of the −35 and −10 boxes is indicated by the two headed arrows. The first base of the formed mRNA is also shown.

FIG. 2 β-galactosidase synthesis in strain JJ6 detected by SDS-PAGE. The number above each lane represents the samples taken at specific intervals (in hours), accordingly with the specific expression time (See text). LacZ protein (116 kDa) was used as the molecular marker.

DETAILED DESCRIPTION

Definitions

The aprE promoter in its wild type form refers to the area that RNA polymerase recognizes and uses to start transcription and includes 2 boxes at −35 and −10 as shown in FIG. 1. Other elements shown around the −35 and −10 boxes, such as, the spacer between the −35 and −10 box, and downstream (3') of the −10 box, down to +40, play an important role in promoter strength. As used herein, the term "mutant aprE promoter" refers to an aprE promoter having a modification in the −35 box and may have additional modifications in the spacer region, the region upstream of the −35 box, in the −10 box and the region downstream of the −10 box. In a preferred embodiment, the mutant aprE promoter has the sequence TGGGTC TTGACA AATATAT- TCCATCTAT TACAAT AAATTCACAGA, designated SEQ ID NO:1. A mutant aprE promoter is one which enhances transcription frequency as measured by the number of mRNA molecules produced per unit time.

As used herein, the genus Bacillus includes all members known to those of skill in the art, including but not limited to *B. subtilis, B. licheniformis, B. lentus, B. brevis, B. stearothermophilus, B. alkalophilus, B. amyloliquefaciens, B. coagulans, B. ciculans, B. lautus and B. thuringiensis.*

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in a gram-positive host cell. Examples of heterologous proteins include enzymes such as hydrolases including proteases, cellulases, amylases, carbohydrases, and lipases; isomerases such as racemases, epimerases, tautomerases, or mutases; transferases, kinases and phophatases. The protein may be a therapeutically significant protein or peptide, such as growth factors, cytokines, ligands, receptors and inhibitors, as well as vaccines and antibodies. The protein may be a commercially important industrial protein or peptide, such as proteases, carbohydrases such as amylases and glucoamylases, cellulases, oxidases and lipases. The gene encoding the protein may be a naturally occurring gene, a mutated gene or a synthetic gene.

The term "homologous protein" refers to a protein or polypeptide native or naturally occurring in a gram-positive host cell. The invention includes host cells producing the homologous protein via recombinant DNA technology. The present invention encompasses a Bacillus host cell having a deletion or interruption of naturally occurring nucleic acid encoding the homologous protein, such as a protease, and having nucleic acid encoding the homologous protein, or a variant thereof, re-introduced in a recombinant form. In another embodiment, the host cell produces the homologous protein.

DETAILED DESCRIPTION OF THE PREFERRED EMBODIMENTS

The present invention relates to the use of a mutant aprE promoter in methods for the production of proteins. aprE is induced in a natural way at the end of exponential growth, when the maximum biomass is reached, minimizing the possibility of mutations and plasmid segregation. Natural induction avoids the necessity of artificial inducers such as those systems based on chemicals like IPTG, oxygen (Walsh K, Koshland D E Jr. (1985)), or physical induction by heat (Bujard et al. 1983). This natural induction of the aprE gene represents an important economical advantage especially at a large industrial scale due to the simplicity of use in fermentation processes.

The aprE promoter sequence has 17 bp between the −10 and −35 boxes and its −10 box is located 6 bp apart from the transcription start site. Strains were constructed which carried specific mutations affecting: i) the aprE'-lacZ mRNA transcription initiation rate, and ii) the aprE'-subtilisn mRNA transcription initiation rate. Furthermore, the effect of hpr2 and degU32 backgrounds was also analyzed. The individual effect of each of these mutations was examined as well as selected combinations of them.

More than a 100-fold increase in the β-galactosidase activity was obtained and over a 30-fold increase in subtilisn activity was obtained by changing the native −35 box sequence in the aprE promoter into the TTGACA sequence. Without being bound to theory, this modification appears to favor an easier recognition of the promoter region by the RNAP, thus facilitating the formation of the open complex and increasing the rate of its formation.

In a preferred embodiment, the Bacillus species is*Bacillus subtilis* which has been genetically engineered to comprise the mutant aprE promoter having the sequence as shown in SEQ ID NO:1 and nucleic acid encoding desired protein or polypeptide, such as a protease or other enzyme. In another embodiment, the Bacillus host cell further comprises mutations or deletions in endogenous proteases, such as, Apr, Npr, Epr, Mpr for example, or other proteases known to those of skill in the art.

The present invention provides host cells, expression methods and systems for the enhanced production and secretion of desired heterologous or homologous proteins in Bacillus species. In one embodiment, a host cell is genetically engineered to comprise a mutant aprE promoter, and in particular, the mutant aprE promoter having the sequence as shown in SEQ ID NO:1, and to further comprise nucleic acid encoding a desired protein or polypeptide. Nucleic acid encoding the desired protein may be integrated into the host cell genome or be provided on a replicating plasmid. Suitable replicating plasmids for Bacillus are described in Molecular Biological Methods for Bacillus, Ed. Harwood and Cutting, John Wiley & Sons, 1990, hereby expressly incorporated by reference; see chapter 3 on plasmids.

Several strategies have been described in the literature for the direct cloning of DNA in Bacillus. Plasmid marker rescue transformation involves the uptake of a donor plasmid by competent cells carrying a partially homologous resident plasmid (Contente et al., Plasmid 2:555–571 (1979); Haima et al., Mol. Gen. Genet. 223:185–191 (1990); Weinrauch et al., J. Bacteriol. 154(3):1077–1087 (1983); and Weinrauch et al., J. Bacteriol. 169(3):1205–1211 (1987)). The incoming donor plasmid recombines with the homologous region of the resident "helper" plasmid in a process that mimics chromosomal transformation.

Transformation by protoplast is described for *B. subtilis* in Chang and Cohen, (1979) Mol. Gen. Genet 168:111–115; for *B.megaterium* in Vorobjeva et al., (1980) FEMS Microbiol. Letters 7:261–263; for *B. amyloliquefaciens* in Smith et al., (1986) Appl. and Env. Microbiol. 51:634; for *B.thuring-*

*iensis* in Fisher et al., (1981) Arch. Microbiol. 139:213–217; for *B.sphaericus* in McDonald (1984) J. Gen. Microbiol. 130:203; and *B.larvae* in Bakhiet et al., (1985) 49:577. Mann et al., (1986, Current Microbiol. 13:131–135) report on transformation of Bacillus protoplasts and Holubova, (1985) Folia Microbiol. 30:97) disclose methods for introducing DNA into protoplasts using DNA containing liposomes.

The manner and method of carrying out the present invention may be more fully understood by those of skill in the art by reference to the following examples, which examples are not intended in any manner to limit the scope of the present invention or of the claims directed thereto.

EXAMPLE I

Materials and Methods

Site-directed mutagenesis of the transcription regulatory regions of the aprE gene.

Plasmid pT7-aprE was constructed by the cloning of the 509 base pairs (bp) EcoRl-BamHI fragment derived from plasmid pSG35.1 (Ferrari E, Henner D J, Perego M, Hoch J A (1988) Transcription of *Bacillus subtilis* subtilisin and expression of subtilisin in sporulation mutants. J. Bacteriol. 170: 289–295), that contains the aprE promoter and the first eight codons of the structural gene, into the plasmid pT7 (Novagen). This new plasmid was used as a template for single or combinatorial oligonucleotide directed PCR mutagenesis according to the protocol described by Merino et al. (1992) A general PCR-based method for single or combinatorial oligonucleotide-directed mutagenesis on pUC/M13 vectors. Biotechniques 12: 509–510). PCRs were carried out with Taq DNA polymerase (Promega Co.) in a Perkin Elmer PCR System. The nucleotide substitutions introduced into the 5' aprE regulatory region were as follows: A-34→T, C-33→G, T-32→A, A-31→C, A-12→G, G+1→A. The final products of the PCR mutagenesis were verified by determining the nucleotide sequence using the dideoxy chain termination method described by Sanger et al. (1977). These DNAs were digested with EcoRI and BamHI, and cloned into the same restriction sites of the integrative plasmid pSG-PLK. Plasmid pSG-PLK is a pSG35.1 derivative in which the EcoRl-BamHI region has been replaced by the polylinker derived from pUC19, leaving a promoterless lacZ gene. This change in pSG-PLK provides an easier selection of transformants because colonies plated on X-Gal (5-bromo-4-chloro-3-indolyl-β-D-galactopyranoside) agar are blue only if they carry the aprE promoter. Table 1 provides an index to the *B. subtilis* strains constructed.

TABLE 1

| Strain | Description | Reference |
| --- | --- | --- |
| BSR1 | Δnpr hisA glyB | Lab stock |
| BSR2 | Δnpr hisA hpr2 | Lab stock |
| BSR3 | Δnpr glyB degU32 cat | Lab stock |
| BSR6 | BSR1 amyE::pSG35.1 cat | This work |
| JJ3 | BSR6 hpr2 | This work |
| JJ5 | BSR6 degU32 | This work |
| JJ7 | BSR6 hpr2 degU32 | This work |
| JJ1 | BSR1 amyE:: pTTGACA cat | This work |
| JJ2 | JJ1 hpr2 cat | This work |
| JJ4 | JJ1 degU32 | This work |
| JJ6 | JJ1 hpr2 degU32 | This work |

Abbreviations: cat, chloramphenicol acetyltransferase gene; amyE-front, the 5' end of the amyE gene.

EXAMPLE II

Transcription Initiation

Characteristics of the wild type aprE regulatory region (rraprE-WT) include a promoter with an almost perfect $\sigma^A$ consensus sequence in its -10 box (TAcAAT); the -35 region has only two of the six nucleotides located at the consensus sequence (TactaA); the presence of 17 bp between the -10 and -35 regions; and the presence of an AT rich sequence upstream the -35 box, that is important for the recognition of the a subunit of the RNA polymerase (RNAP) (Ross et al. 1993 A third recognition element in bacterial promoters: DNA binding by the alpha subunit of RNA polymerase. Science 262: 1407–1413.). Based on these characteristics, a site directed mutagenesis at the -35 region of the promoter sequence was performed in order to obtain the -35 consensus region for genes recognized by the $\sigma^A$ factor of B. subtilis. Considering that the -35 region of the aprE regulatory region has only two of the six nucleotides present in the consensus sequence, four nucleotide changes (ACTA -34 to -31 →TGAC) were introduced. This modified regulatory region is designated herein as rraprE-TTGACA. This mutation was cloned upstream of the lacZ reporter gene and integrated into the amy locus of the *B. subtilis* chromosome, generating strain JJ1. The β-galactosidase activity of this strain was assayed; the modifications of the -35 promoter box produced a 106-fold increase in its β-galactosidase activity with respect to the parental BSR6 strain that carries the aprE wild type promoter (See Table 2 and FIG. 2).

TABLE 2

| Strain | Maximum specific activity U/mgprot[A] | Relative activity with respect to BSR6 | Relative activity with respect to JJ1 |
| --- | --- | --- | --- |
| BSR6 | 2 452 | 1X | .009X |
| JJ3 | 8 105 | 3.3X | .03X |
| JJ5 | 89 000 | 36.3X | 0.3X |
| JJ7 | 162 330 | 66X | 0.6X |
| JJ1 | 261 360 | 106X | 1X |
| JJ2 | 472 090 | 192X | 1.8X |
| JJ4 | 335 810 | 137X | 1.3X |
| JJ6 | 712 300 | 290X | 2.7X |

Table 2 shows a comparison of the β-galactosidase levels obtained in different strains.
[A]The values shown are the averages of three independent experiments.
The activity assayed is β-gal expressed from the aprE'-lacZ fusion.

EXAMPLE III

Effect of hpr2 and degU32 Backgrounds on aprE'-lacZ Expression

It has been reported that the hpr2 mutation increases the expression levels of subtilisin. This mutation is a deletion of a DNA segment of 359 bp of the structural gene, that decreases 65% its activity (Perego and Hoch 1988 Sequence Analysis and Regulation of the hpr locus, a Regulatory Gene for Protease Production and Sporulation in *Bacillus subtilis*. J. Bacteriol. 170: 2560–2567). degU32 is a mutation that consists in the substitution A2006→T that changes an histidine residue to a leucine residue in the $12^{th}$ amino acid of the protein (Henner et al. 1988 Localization of *Bacillus subtilis* sacU(Hy) mutations to two linked genes with similarities to the conserved procaryotic family of two-component signalling systems. J. Bacteriol. 170: 5102–9). This mutation increases the DegU-PO$_4$ state, hence it carries out its activating effect for a longer time.

With the aim of constructing an overproducer strain, the hpr2 and degU32 genotypes were transferred into BSR6 (BSR1 amyE::pSG35.1) and JJ1 (BSR1 amyE::pTTGACA)

strains in an individual and combinatory fashion (see Table 1). The data for the β-galactosidase activities of these strains are displayed in Table 2. With the hpr2 mutation, JJ3 strain yielded an increase of 3.3 fold while JJ2 strain had an increase of 1.8 fold. Strains JJ5 and JJ4, carrying the degU32 genetic background, had increases of 36.3 and 1.3 fold, respectively. The activity levels obtained in strains JJ7 and JJ6, carrying both degU32 and hpr2 genetic backgrounds, were respectively 66 and 2.7 fold when compared to their parental strains.

Similar results have been obtained in homologous strains JJ3 by Bolaños (2.8 fold) and Olmos et al (4.6 fold) (Bolanos 1994 In master thesis: Sobreproduccion de la enzima β-galactosidasa de *Escherichia coli* en *Bacillus subtilis*. Instituto de Biotecnologia, Universidad Nacional Autonoma de Mexico. Cuernavaca, Mor. Mexico.; Olmos et al. 1996, A functional SpoOA is required for maximal aprE expression in *Bacillus subtilis*. FEBS Lett. 381: 29–31). A functional SpoOA is required for maximal aprE expression in *Bacillus subtilis*. FEBS Lett. 381: 29–31). The hpr2 mutation carries out its effect not only with the wild type promoter, but also with the modified promoter in strain JJ2.

Without wanting to be bound by theory it is conceivable that the mutations degU32 and the change to the −35 consensus favor the recognition of the promoter sequence by the RNAP in a similar way, and may assist and stabilize the formation of the DNA-RNAP open complex.

In summary, several elements have been analyzed in the process to construct overproducer *B. subtilis* strains. The most significant change occurred when the mutant promoter sequence shown in FIG. 1 was incorporated into the regulatory region of the aprE gene, yielding strain JJ1. This change permitted an increase over 100-fold with respect to the strain considered as the wild type in this study (BSR6). Although strain JJ6 reached the highest level of β-galactosidase activity, it has several pleiotropic effects, in contrast to JJ1 strain.

EXAMPLE IV
Measurement of β-galactosidase Synthesis

This example illustrates the production of the heterologous protein, β-galactosidase In order to have a direct estimation of the synthesis of the β-galactosidase protein for establishing a direct relationship with the activity level found in our overproducer strains, we analyzed the total protein profile by SDS-PAGE of the strain JJ6 (BSR1 amyE::pTTGACA hpr2 degU32), the strain with the highest level of β-galactosidase activity. Strain JJ6 was grown in Shaeffer medium and samples were taken at regular intervals. The cell-free extracts obtained by sonication were analyzed by SDS-PAGE and stained with Coomassie brilliant blue (FIG. 2). β-galactosidase protein was observed as a band with a molecular mass of 116 kDa. The sporulation process started five hours after the inoculation. At this time, the expression of the recombinant protein started and reached its maximun two hours later, corresponding roughly to 10% of the total intracellular protein.

EXAMPLE V

This Example describes the construction of a *Bacillus subtilis* host cell containing the mutant aprE promoter. The level of the extracellular protease AprE produced after modifying the aprE promoter was quantified using strain OS4. For comparison, several other strains that carried the wild type aprE gene were analyzed under the same conditions. The differences among these strains are that they contain mutations that are known to enhance aprE expression (Valle and Ferrari, supra). The results of this analysis are shown in Table 3. As can be seen, compared with the wild type strain, the OS4 strain produced 32.7 fold more AprE. On the other hand, compared with the strain carrying the wild type aprE and the degU, scoC mutations, strain OS4 produced 50% less subtilisn. Considering the results obtained with the expression of lacZ presented in Table 2, it may be possible to further increase the production of subtilisn by using the hpr2 and/or degU mutation(s). The results obtained with strain OS4 indicate that the modified aprE promoter can be used also to overproduce homologous proteins that are secreted to the media.

Construction of a PCR fusion sequence, designated herein as OS4

OS4 PCR fusion was constructed in 3 steps: 1) amplification of 2 separate fragments by PCR from Bacillus subtilis 168 chromosomal DNA; 2) assembly of 2 purified PCR fragments in PCR type process without primers; and 3) amplification of the assembled product by PCR with OSBS-1 and OSBS-8 end primers.

1). Chromosomal DNA of *Bacillus subtilis* 168 was used as a template for amplification of aprE gene locus using 2 sets of primers. The first pair of primers consisted of OSBS-1 (5'-ATATGTGGTGCCGAAACGCTCTGGGGTAAC-3' SEQ ID NO: 2) located from 1101.821 kb to 1101.851 kb on the Bacillus chromosome and Stu-1 (5'-CTCAAAAAAATGGGTCTACTAAAATATTATTCCAT CTATTACAATAAATTCA-3' SEQ ID NO: 3) located from 1105.149 kb to 1105.098 kb. The amplified fragment was 3.327 kb and contained the following genes: truncated yhfL', yhfM, yhfN and aprE promoter area, see Kunst et al., 1997, Nature, vol 390, pages 249–256 for a description of the *B. subtilis* genome.

The second pair of primers consisted of Stu-2 (5'-TGAATTTATTGTAATAGATGGAATAATATTTTAGTA GACCCATTTTTTTGAG-1-3' SEQ ID NO: 4) located from 1105.098 kb to 1105.149 kb on the chromosome and OSBS-8(5'-CTTTTCTTCATGCGCCGTCAGCTTTTTCTC-3' SEQ ID NO:5) located from 1107.733 kb to 1107.704 kb. The amplified fragment was 2.635 kb and contained the following: promoter area of aprE, yhfO, yhfP and truncated yhfQ'. Both PCR products were overlapping in the promoter area. Stu-1 and Stu-2 complementary primers were used for introduction of 4 mutations in −35 area of aprE promoter, where TACTAA was replaced with TTGACA sequence. Perkin Elmer GeneAmp XL PCR kit containing rTth polymerase was used according to the manufacturer instructions for all PCRs. PCR reactions were performed in 100 ul volume.

DNA—2–5 ul
3.3×XL Buffer II—30 ul
10 mM dNTP Blend—3 ul
25 mM Mg(OAc)2—4 ul
b 25uM OSBS-1 primer (or OSBS-8)—2 ul
25 uM Stu-1 primer (or Stu-2)—2 ul
2U/ul rTth polymerase—2 ul
Water—adjust to 100 ul The PCR conditions were: 95° C.—30 sec, 54° C.—30 sec, 68° C.—3 min for 30 cycles. The obtained PCR fragments, 3.327 kb and 2.635 kb, were purified with QIAGEN PCR purification kit according to the manufacturer instructions and used for PCR assembly.

2). 5 ul aliquots of purified PCR fragments were mixed together and added into fresh PCR mix that didn't contain primers. The total volume of PCR mixture was 100 ul with components as described above. The PCR assembly conditions were: 95° C.—30 sec, 52° C.—30 sec, 68° C.—2 min for 10 cycles.

3). After 10 cycles of PCR, the assembly mixture was supplemented with OSBS-1 and OSBS-8 primers and PCR amplification was run for 15 additional cycles. The PCR conditions this time were: 95° C.—30 sec, 52° C.—30 sec, 68° C.—5 min. The desired 5.962 kb product was obtained, named OS4-Pcons-aprE and used for transformation of OS1 competent cells to generate OS4 strain.

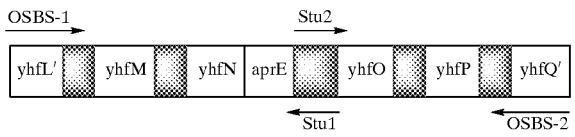

Transformation of OS1 competent cells.

OS1 strain was generated from *Bacillus subtilis* strain designated BG2822 by replacing the aprE gene with a kanamycin gene. The kanamycin gene was inserted into positions from 1103.484 Kb to 1105.663 Kb on the Bacillus chromosome. Therefore, the strain didn't form any halos on LB+1.6% skim milk plates. BG2822 is a derivative of *Bacillus subtilis* 168 which has an npr delete, a deletion in the gene coding for neutral protease (J. Bacteriol. 1984, vol. 160, pg. 15–21).

Since OS4-Pcons-aprE PCR fusion didn't carry any antibiotic marker, the fusion was introduced to the cells by congression. 20 uls of PCR product were mixed with 1 ul (~10 nM) pBS19 plasmid and used for transformation of OS1. The transformation mixture was plated on LB+1.6% skim milk+5 ug/ml cmp plates. Next day, halo-forming colonies were picked and plated for single colonies. The colony purification was performed twice. 5 individual clones were analyzed by sequencing of aprE promoter region. All of them had consensus sequence at –35 region of aprE promoter.

TABLE 3

| Strain designation | Relevant genotype | Relative aprE expression level |
|---|---|---|
| BG2822 | Wild type, nprE- | 1 |
| OS4 | $P_{aprE}$ TTGACA[1] | 32.71 |
| BG2790 | DegU$^{32}$, scoC | 65.14 |
| BG2805 | DegU$^{32}$, scoC, degQ | 22.16 |
| BG2810 | scoC, degQ | 2.43 |

TABLE 3-continued

| Strain designation | Relevant genotype | Relative aprE expression level |
|---|---|---|
| BG2815 | scoC | 1.43 |
| BG2817 | DegU$^{32}$ | 20.54 |
| BG2820 | DegU$^{32}$2, degQ | 8.92 |
| BG2821 | degQ | 2.98 |

Table 3. Expression of the aprE gene in different Bacillus strains. AprE activity was measured after 48 hrs. of growth in 2x SMB medium.
[1]In this strain the –35 region of the aprE promoter was changed to the consensus sequence TTGACA.

EXAMPLE VI

Example XI provides the protocols for culture growth of modified *B.subtilis* strains and protease detection
Culture growth
Pre-cultures of the strains were grown in 2 ml of LB (Luria-Bertani media) to an OD of ~0.35 at A620 nm. The pre-cultures were then aliquoted into 96 well microtiter plate (Costar, Cat #3598), four wells per strain. A 96 well filter bottom plate (Millipore, MAGVN2250) containing 200 ul of 2×SMB growth media was inoculated from the pre-cultural plate using a sterile 96 well stamp. The plate was grown at 37 C., 280 RPM in a humidified shaker box, and assayed for protease activity after 20 and 48 hours of growth.
Luria-Bertani Broth
To 950 mls of deionized water add:
Bacto-trytone 10 g
Bacto-yeast extract 5 g
NaCl 10 g
The solutes were shaken until dissolved. The pH was adjusted to 7.4 with 5 N NaOH ('0.2 ml). The volume of solution was adjusted to 1 liter with deionized water and sterilized by autoclaving for 20 minutes at 15 lb/sq in, on a liquid cycle.
Protease Assay
Aliquots from the growth plate were taken and diluted into Tris buffer (100 mM pH 8.6, 0.005% Tween 80) in a 96 well microtiter plate using a Multispence (Asys Hitech). The protease activity of this plate was determined by dispensing an aliquot from the diluted plate into 96 well plate containing Tris buffer and substrate (1 mg/ml Suc AAPF pNA— Bachem Cat # L-1400). The reaction was then read on a 96 well plate reader (Molecular Devices, SpectraMax 250). The protease concentration of each well was determined based on the rate of substrate hydrolysis, a conversion factor of 0.02 mg/U and the dilution factor.

We claim:

1. An isolated mutant aprE promoter comprising a modification in any of the nucleotides of the −35 consensus box of the wild type promoter as illustrated in FIG. 1.

2. The isolated mutant aprE promoter having the nucleotide sequence as given in SEQ ID NO: 1.

3. An expression vector comprising an isolated mutant promoter, wherein said mutant promoter is a mutant aprE promoter and includes a modification in any of the nucleotides of the −35 box of the wild type promoter as illustrated in FIG. 1.

4. The expression vector of claim 3 wherein the isolated mutant aprE promoter has the nucleotide sequence as shown in SEQ ID NO:1.

5. (Twice Amended) A host cell comprising an isolated mutant aprE promoter, wherein said mutant aprE promoter includes a modification in any of the nucleotides of the −35 consensus box of the wild type promoter as illustrated in FIG. 1.

6. The host cell of claim 5 wherein the mutant aprE promoter has the nucleotide sequence as given in SEQ ID NO:1.

7. The host cell of claim 5, wherein said host cell is from a Bacillus species.

8. The host cell of claim 7 further comprising a nucleic acid sequence encoding a desired protein linked to the mutant aprE promoter.

9. The host cell of claim 8 wherein said desired protein is homologous to said host cell.

10. The host cell of claim 8 wherein said desired protein is heterologous to said host cell.

11. The host cell of claim 8 wherein said desired protein is selected from the group consisting of proteases, cellulases, amylases, carbohydrases, lipases, isomerases, transferases kinases and phophatases.

12. The host cell of claim 7 wherein said Bacillus species is selected from the group consisting of *B. licheniformis, B. lentus, B. brevis, B. stearothermophilus, B. alkalophilus, B. amyloliquifaciens, B. coagulans. B. circulans, B. lautus* and *B. thuringiensis.*

13. An isolated mutant aprE promoter comprising a modification in one or more of the nucleotides of the −35 consensus box compared to a wild-type aprE promoter wherein said mutant aprE promoter enhances transcription frequency as measured by the number of mRNA molecules produced per unit of time.

14. An expression vector comprising the isolated mutant aprE promoter of claim 13.

15. The mutant aprE promoter of claim 1 further comprising a modification in the 17 base pair spacer region of the wild type promoter as illustrated in FIG. 1.

16. The mutant aprE promoter of claim 1 further comprising a modification in the nucleotides of the −10 consensus box of the wild-type promoter as illustrated in FIG. 1.

17. The expression vector of claim 3, further comprising a nucleic acid encoding a desired protein, wherein expression of said desired protein is under the control of said mutant aprE promoter.

18. The expression vector of claim 17, wherein said desired protein is selected from the group consisting of proteases, cellulases, amylases, carbohydrases, lipases, isomerases, transferases, kinases and phophatases.

19. The expression vector of claim 17, wherein the protease is subtilisin.

20. The expression vector of claim 4 further comprising a nucleic acid encoding a desired protein, wherein expression of said desired protein is under the control of said mutant aprE promoter.

21. A host cell comprising the expression vector of claim 20.

22. The host cell of claim 7, wherein said host cell is a *Bacillus subtilis* host cell.

23. The host cell of claim 6, wherein said host cell is a Bacillus species selected from the group consisting of *B. licheniformis, B. lentus, B. brevis, B. stearothermophilus, B. alkalophilus, B. amyloliquifaciens, B. coagulans, B. circulans, B. lautus, B. thuringiensis* and *B. subtilis.*

* * * * *